United States Patent
Sas et al.

(10) Patent No.: US 7,368,475 B2
(45) Date of Patent: May 6, 2008

(54) FURANOSE-TYPE BICYCLIC CARBOHYDRATES WITH BIOLOGICAL ACTIVITY

(75) Inventors: Benedikt Sas, Stekene (BE); Johan Van hemel, Antwerp (BE); Jan Vandenkerckhove, Zichem (BE); Eric Peys, Balen (BE); Johan Van der Eycken, Ninove (BE); Steven Van Hoof, Genk (BE)

(73) Assignee: Kemin Pharma BVBA, Des Moines, IA (US)

( * ) Notice: Subject to any disclaimer, the term of this patent is extended or adjusted under 35 U.S.C. 154(b) by 431 days.

(21) Appl. No.: 10/760,647

(22) Filed: Jan. 20, 2004

(65) Prior Publication Data

US 2004/0220251 A1     Nov. 4, 2004

Related U.S. Application Data

(60) Provisional application No. 60/454,099, filed on Mar. 12, 2003.

(51) Int. Cl.
*A01N 43/08* (2006.01)
*A61K 31/34* (2006.01)
*C07D 321/00* (2006.01)

(52) U.S. Cl. .................... 514/461; 549/200
(58) Field of Classification Search .............. 536/1.11; 514/25, 461; 549/215, 348, 354, 369, 200
See application file for complete search history.

(56) References Cited

U.S. PATENT DOCUMENTS 5,098,927 A * 3/1992 Takatsuki et al. ............ 514/425
5,672,501 A * 9/1997 Matulic-Adamic et al. . 435/325
6,121,296 A * 9/2000 Schramm et al. ............ 514/343

FOREIGN PATENT DOCUMENTS

WO    WO 03/082846 A1    10/2003
WO    WO 2004/014929 A1    2/2004

OTHER PUBLICATIONS

Database Caplus on STN, AN 2001:544756. Espinola et al. "Synthetic Flux-Promoting Polyether Modstl:Cation Flux Dependence on Polyoxyethylene Chain Length", Isreal Journal of Chemistry. 2000, vol. 40, Issue 3-4.
Khalili et al., Pharmacokinetics and metabolism of the Novel Synthetic C-Nucleoside, 1-(2-deoxy-beta-D-ribofuranosyl)-2, 4-difluoro-5-iodobenzene: a potential mimic of 5-iodo-2-deoxyuridine, Biopharmeutics and Drug Disposition, 2002, vol. 23, p. 105-113 See p. 105, col. 2 and p. 106, figure 1.
Sharma et al., Synthesis and biological activity of 4-(beta-D-Ribofuranosyl)-1, 3-dihydroxybenzene ("1,3-Dideazauridine"), Journal of Medicinal Chemistry, 1975, vol. 18 No. 5, pp. 473-476.
Polt et al., Erythrose Sesqui-Acetals as Electrophiles. 2-Deoxy-C-Nucleosides from D-Glucose, Tetrahedron Letter, 1991, vol. 32, No. 37, pp. 4831-4834.
Tadano et al., Total Synthesis of (+)-Gonlothalenol [(+)-Altholactone], a Novel Bioactive Tetrahydrofurano-2-pyrone, Chemistry Letters, 1988, vol. 1, pp. 111-114.

* cited by examiner

Primary Examiner—James O. Wilson
Assistant Examiner—Paul V. Ward
(74) Attorney, Agent, or Firm—Kent Herink (57) ABSTRACT

The synthesis and study of biological activity of a series of new molecules with potential antimicrobial activity are described. The molecules are bicyclic carbohydrates, based on furanose sugars. Their antimicrobial activity against viruses is demonstrated, next to cytostatic effects. Significantly, a high and selective activity against Cytomegalovirus was observed.

6 Claims, 2 Drawing Sheets

FURANOSE-TYPE BICYCLIC CARBOHYDRATES WITH BIOLOGICAL ACTIVITY

This application claims priority to U.S. patent application Ser. No. 60/454,099, filed Mar. 12, 2003.

BACKGROUND TO THE INVENTION

The invention relates generally to bicyclic carbohydrates and, more specifically to furanose-type bicyclic carbohydrates that have antiviral and cytostatic activity.

Cytomegalovirus, or CMV, is found universally throughout all geographic locations and socio-economic groups, and infects between 50% and 85% of adults in the United States by 40 years of age. CMV is also the virus most frequently transmitted to a developing child before birth. CMV infection is more widespread in developing countries and in areas of lower socio-economic conditions. For most healthy persons who acquire CMV after birth there are few symptoms and no long-term health consequences. Some persons with symptoms experience a mononucleosis-like syndrome with prolonged fever, and a mild hepatitis. Once a person becomes infected, the virus remains alive, but usually dormant within that person's body for life. Recurrent disease rarely occurs unless the person's immune system is suppressed due to therapeutic drugs or disease. Therefore, for the vast majority of people, CMV infection is not a serious problem.

However, CMV infection is important to certain high-risk groups. Major areas of concern are (1) the risk of infection to the unborn baby during pregnancy, (2) the risk of infection to people who work with children, and (3) the risk of infection to the immuno-compromised person, such as organ transplant recipients and persons infected with human immunodeficiency virus (HIV).

CMV is a member of the herpesvirus group, which includes herpes simplex virus types 1 and 2, varicella-zoster virus (which causes chickenpox), and Epstein-Barr virus (which causes infectious mononucleosis). Infectious CMV may be shed in the bodily fluids of any previously infected person, and thus may be found in urine, saliva, blood, tears, semen, and breast milk. The shedding of virus may take place intermittently, without any detectable signs, and without causing symptoms.

Most infections with CMV are not diagnosed because the virus usually produces few, if any, symptoms and tends to reactivate intermittently without symptoms. However, persons who have been infected with CMV develop antibodies to the virus, and these antibodies persist in the body for the lifetime of that individual. A number of laboratory tests that detect these antibodies to CMV have been developed to determine if infection has occurred and are widely available from commercial laboratories. In addition, the virus can be cultured from specimens obtained from urine, throat swabs, and tissue samples to detect active infection.

Currently, no treatment exists for CMV infection in the healthy individual. Antiviral drug therapy is now being evaluated in infants. Ganciclovir (DHPG) treatment is used for patients with depressed immunity that have either sight-related or life-threatening illnesses. Other products that are used to treat CMV infections are the nucleoside analogue (S)—HPMPC (Cidofovir) and the phosphonate analogue Foscarnet (Foscavir). However, all these treatments have drawbacks such as toxicity problems and the building up of resistance. Vaccines are still in the research and development stage.

Recently, researchers all over the world are getting more and more aware that sugars play an extremely important role in living creatures. It turns out that sugars are involved in almost every aspect in biology, from recognizing pathogens, to blood clotting, to enabling sperm to penetrate an ovum. Biologists are only just beginning to come to grips with these important sugars, but as they do they are finding themselves having to rethink long-held ideas about how life works (K. Schmidt; Sugar rush. *New Scientist*, (26 Oct. 2002) 34-38). This importance of sugars is demonstrated by the fact that in addition to the terms "genomics" and "proteomics", the term "glycomics" is now being used.

This underlines the importance of product groups containing sugars, to which also the bicyclic carbohydrate derivatives described in this specification belong. In other work, the synthesis and properties of a series of bicyclic carbohydrates based on pyranose sugars has been described.

SUMMARY OF THE INVENTION

Figure 1:
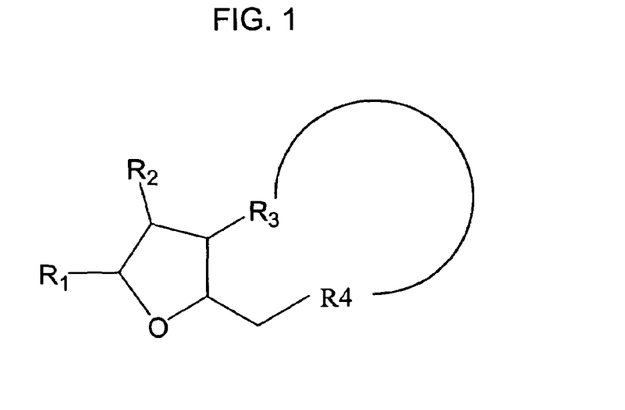
FIG. 1 is a diagrammatic view of the general structure of the compounds of the present invention.

The molecules described herein belong to a class of protected furanose derivatives. The general structure of this class of compounds is:

wherein $R_1$ may be alkyl, aryl, O-alkyl, O-aryl, S-alkyl, S-aryl, OH, OR, SR, $NH_2$, $N_3$, halogens, —OOCR, COOR, and the like; $R_2$ may be hydrogen, hydroxyl, aliphatic and aromatic ethers, aliphatic and aromatic esters, and the like; $R_3$ may be alkyl, aryl, O-alkyl, O-aryl, S-alkyl, S-aryl, OH, OR, SR, $NH_2$, $N_3$, halogens, —OOCR, COOR, acetal rings and siloxane rings and the like; $R_4$, may be alkyl, aryl, O-alkyl, O-aryl, S-alkyl, S-aryl, OH, OR, SR, $NH_2$, $N_3$, halogens, —OOCR, COOR, acetal rings and siloxane rings, and the like; and wherein $R_3$ and $R_4$ may form an acetal ring; and wherein X is selected from the group comprising O, N and S. R is H or any organic group

DETAILED DESCRIPTION OF PREFERRED EMBODIMENTS

TABLE 1

Examples of molecules of the described product class

| Compound | Structure | $R_1$ | $R_2$ | $R_3$ | $R_4$ |
|---|---|---|---|---|---|
| Compound A1 | (structure) | —Ph | —OH | —H | —H |
| Compound A2 | (structure) | —Ph | —OH | —OSi(i-Pr)$_2$OSi(i-Pr)$_2$O— | |
| Compound A3 | (structure) | —Ph | —OMe | —OSi(i-Pr)$_2$OSi(i-Pr)$_2$O— | |
| Compound A4 | (structure) | —Ph | —OMe | —H | —H |
| Compound A5 | (structure) | —Ph | —OMe | —OCH(Ph)O— | |
| Compound A6 A + B | (structure) | —Ph | —H | —OSi(i-Pr)$_2$OSi(i-Pr)$_2$O— | |
| Compound A7 | (structure) | —Ph | —H | —OAc | —OAc |
| Compound A8 | (structure) | —Ph | —H | —OH | —OH |

TABLE 1-continued

Examples of molecules of the described product class

| Compound | Structure | $R_1$ | $R_2$ | $R_3$ | $R_4$ |
|---|---|---|---|---|---|
| Compound A9 | | | —OC(CH$_3$)$_2$O— | —OBn | —OBn |

General Scheme of Synthesis

Synthesis of β-D-1-deoxy-1-phenylribofuranose benzylidene acetal derivatives

Figure 2:
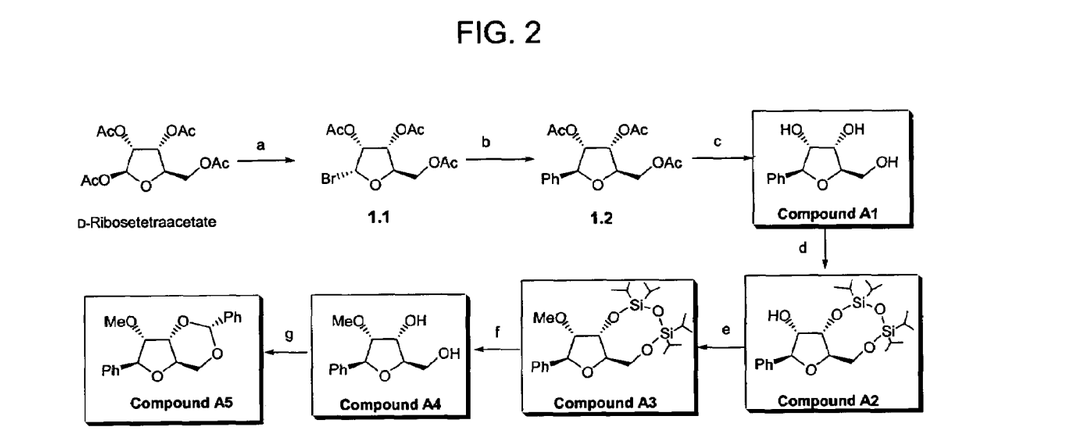
FIG. 2 is a diagrammatic representation of a scheme of synthesis of a first set of compounds of the present invention.

The commercially available β-D-ribose tertraacetate is converted into its α-bromo derivative (Compound 1.1 in FIG. 2) by treatment with HBr in acetic acid. Introduction of the phenyl group with phenylmagnesium bromide results in the formation of Compound 1.2. The acetyl groups were subsequently removed by treatment with potassium carbonate in methanol. Protection of the free hydroxyl functions at $C_3$ and $C_5$ was achieved by treatment of Compound A1 with 1.2 eq. 1,3-dichloro-1,1,3,3-tetraisopropyldisiloxane, giving Compound A2 in 78% yield. After methylation of the free hydroxyl group at $C_2$ with iodomethane, Compound A3 was deprotected to Compound A4 using tetrabutylammonium fluoride. In the last step the acetal formation was accomplished using α,α-dibromotoluene.

Synthesis of β-D-1-deoxy-1-phenylribofuranose derivatives.

Figure 3:
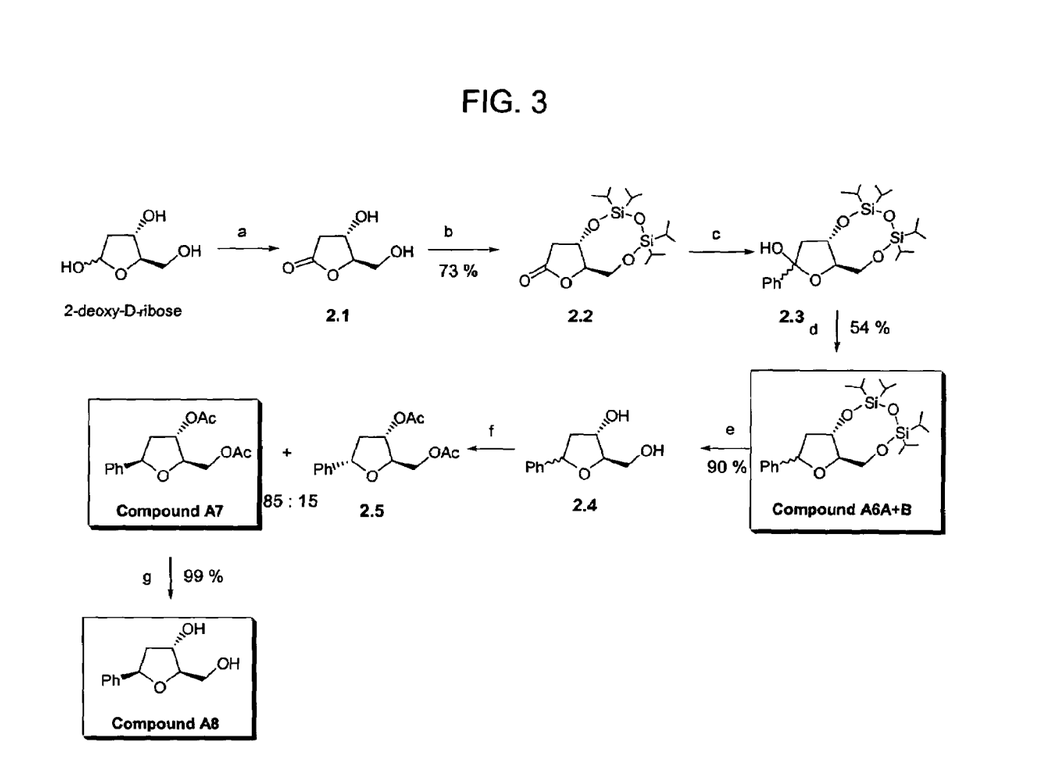
FIG. 3 is a diagrammatic representation of a scheme of synthesis of a second set of compounds of the present invention.

2-Deoxy-D-ribose, which is commercially available, is oxidized to its 1-oxo derivative (Compound 2.1 in FIG. 3) by treatment with Br$_2$ in water. After protection of the free alcohol functions at $C_3$ and $C_5$ with 1,3-dichloro-1,1,3,3-tetraisopropyldisiloxane, 2.2 was reacted with phenyllithium, which introduced the phenyl moiety at $C_1$. Removal of the $C_1$ hydoxyl group using Et$_3$SiH in BF$_3$.Et$_2$O yielded the diastereomeric mixture Compound A6 A+B, which could not be separated by chromatography. After removal of the silyl protecting group with TBAF and acetylating the free hydroxyls of 2.4, the two diastereomers of Compound A7 could be separated. The β-diastereomer was then treated with potassium carbonate in methanol, giving Compound A8 in 99% yield.

Figure 4:
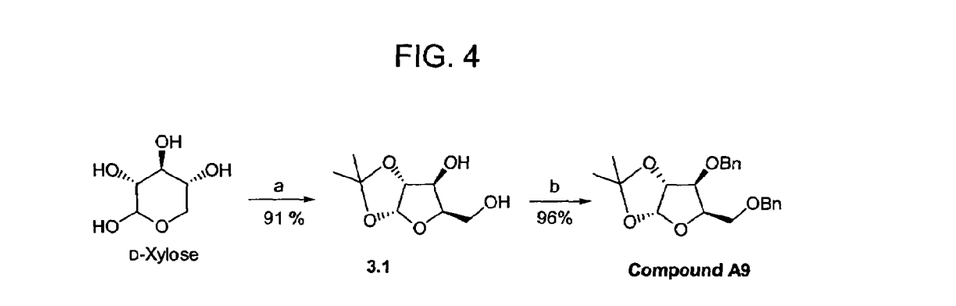
FIG. 4 is a diagrammatic representation of a scheme of synthesis of a third set of compounds of the present invention.

Synthesis of α-D-xylofuranose derivative Commercially available D-xylanose is treated with acetone in acidic conditions, resulting in the 1,2-isopropylidene derivative (Compound 3.1 in FIG. 4) in 91% yield. The free hydroxyl functions were then benzylated by adding NaH and benzylbromide which gave Compound A9 in 96% yield.

Detailed Synthesis of the Molecules

All reactions were carried out in dry solvents under inert atmosphere (argon or nitrogen) in dry glassware, unless stated otherwise. The reactions were monitored by thin layer chromatography (Merck silicagel 60F254 0.25 mm thickness).

Tetrahydrofuran, diethyl ether, dimethyl ethylene glycol and toluene were distilled from sodium/benzophenon. Methylene chloride was distilled from phosphorpentoxide. Triethylamine, diisopropylethylamine and pyridine were distilled from calciumhydride. Dimethylformamide was distilled from calciumhydride and stored on molecular sieves (4 Å).

All products were purified by flash chromatography on silicagel (Merck silicagel 60F254) or by HPLC on an Rsil-phase with RI detection, unless stated otherwise.

Melting points were measured with a melting microscope and are not corrected. $R_f$ values are referring to Merck silica 60F254. Optical rotation values of homochiral products were measured with a Perkin-Elmer 241 polarimeter. IR spectra were recorded on a Perkin-Elmer 1600 series FTIR. Mass spectra were recorded on an "atmospheric pressure electrospray-ionization" Hewlett-Packard 1100 MSD mass detector. $^1$H-NMR spectra were recorded at 500 MHz (Brücker AN-500). $^{13}$C-NMR spectra were recorded at 125 MHz (Brücker AN-500).

A. Synthesis of α-D-1-Deoxy-1-bromo-ribofuranose-2,3,5-triacetate (Compound 1.1)

β-D-Ribofuranose-1,2,3,5-tetraacetate (100 mg, 0.314 mmol) was dissolved in a 33 wt % solution of hydrobromic acid in acetic acid (50 ml). The reaction mixture was stirred at room temperature for 30 min. Subsequently the mixture was concentrated in vacuo, followed by azeotropic rotavapory evaporation with toluene (3×50 ml) to remove all acetic acid. The residue was used in the next reaction step without further purification.

B. Synthesis of β-D-1-Deoxy-1-phenyl-ribofuranose triacetate (Compound 1.2)

To a solution of phenylmagnesium bromide (3M solution in diethyl ether, 9.5 eq, 100 ml) in diethyl ether (250 ml), cooled to 0° C., was added a solution of β-D-1-deoxy-1-bromo-ribofuranose-2,3,5-triacetate (theoretically 10.68 g) in diethyl ether (250 ml) via canula. The reaction mixture was stirred at 0° C. for 15 min., after which the temperature was allowed to reach room temperature, and stirring was continued for 3 days. Subsequently, the reaction mixture was poured out in water (1 l) and acetic acid (100 ml). Layers were separated, and the organic layer was extracted with water (3×250 ml). The aqueous layers were combined and concentrated in vacuo. Azeotropic rotavapory evaporation with toluene made sure all traces of water and acetic acid were removed. The residue was dissolved in pyridine (250 ml) and acetic anhydride (170 ml), while cooling to 0° C. Then 4-N,N-dimethylaminopyridine (385 mg, 3.15 mmol) was added. After 1 h the reaction mixture was allowed to reach room temperature and stirring was continued overnight. Work-up was started by pouring out the reaction mixture in a saturated sodium carbonate solution (1 l), followed by dilution with ethyl acetate and separation of the two phases. The organic layer was washed with 1N HCl solution (4×500 ml) and brine (500 ml), dried over MgSO$_4$ and concentrated in vacuo, to yield 8.58 g of a brown oil. Purification by column chromatography (230-400 mesh silica, pentane: ether 6:4) yielded 1.99 g of pure β-isomer (19%) and 2.46 g of impure α-isomer.

Formula: $C_{17}H_{20}O_7$

Molecular weight: 336.34 $R_f$: 0.17 (pentane: ether 6:4) $[\alpha]_D^{20}$=−28.5°; $[\alpha]_{436}^{20}$=−61.4° (c=1.00 in chloroform) IR (KBr) (cm$^{-1}$): 3032 (m), 2940 (m), 2894 (m), 1747 (s), 1497 (m), 1458 (m), 1438 (m), 1374 (s), 1230 (s), 1093 (s), 1058 (s), 1040 (s), 1021 (s), 934 (m), 902 (m), 763 (m), 735 (m), 700 (m) EI-MS: (m/z) 43 (100), 85 (10), 107 (8), 157 (32), 174 (12), 216 (3), 276 (2), 336 (<1) [M$^+$] $^1$H-NMR (500 MHz, CDCl$_3$): δ (ppm) 7.40-7.30 (5H, m), 5.28 (1H, s), 5.10 (1H, dd, app. t, J=5.6, 4.9 Hz), 5.01 (1H, d, J=6.4 Hz), 4.45 (1H, dd, J=11.8, 2.9 Hz), 4.34 (1H, ddd, app dt, J=4.9, 4.3, 2.9 Hz), 4.29 (1H, dd, J=11.8, 4.3 Hz) $^{13}$C-NMR (125 MHz, CDCl$_3$): δ (ppm) 171.1 (q), 170.2 (q), 170.1 (q), 138.5 (q), 129.0 (t), 128.8 (t), 126.4 (t), 82.6 (t), 80.2 (t), 77.1 (t), 72.0 (t), 64.0 (s), 21.3 (p), 21.1 (p), 21.0 (p)

C. Synthesis of β-D-1-Deoxy-1-phenyl-ribofuranose (Compound A1)

To a solution of KPE00001076 (1.87 g, 5.57 mmol), in a 1:1 mixture of methanol and tetrahydrofuran (56 ml), was added potassium carbonate (192 mg, 0.25 eq). The reaction was stirred at room temperature for 2 hours. The reaction mixture was then concentrated in vacuo to give a yellow-orange foam (1.38 g). This was purified by column chromatography (230-400 mesh silicagel, dichloromethane: methanol 95:5). The product was applied on the column by concentrating it on silicagel. In this way 1.13 g of Compound A1 as a white crystalline residue was obtained (97%).

Formula: $C_{11}H_{14}O_4$

Molecular weight: 210.23 $R_f$: 0.17 (CH$_2$Cl$_2$: methanol 95:5) Melting point: 118° C. $[\alpha]_D^{20}$=−26.8° (c=1.00 in methanol) IR (KBr) (cm$^{-1}$): 3283 (br s), 2919 (s), 2861 (s), 1655 (m), 1443 (m), 1384 (m), 1365 (m) 1314 (m), 1208 (m), 1102 (s), 1073 (m), 1049 (m), 1014 (s), 855 (m), 738 (m), 691 (m) ES-MS: (m/z) 233 [M+Na$^+$] $^1$H-NMR (500 MHz, CDCl$_3$): δ (ppm) 7.44 (2H, d, J=7.2 Hz), 7.32 (2H, dd, app. t, J=7.2 Hz), 7.26 (1H, t, J=7.2 Hz), 4.70 (1H, d, J=6.7 Hz), 4.03 (1H, dd, J=5.6, 4.2 Hz), 3.96 (1H, ddd, J=4.9, 4.2, 3.8 Hz), 3.85 (1H, dd, J=6.7, 5.6 Hz), 3.78 (1H, dd, J=11.9, 3.8 Hz), 3.72 (1H, dd, 11.9, 4.9 Hz) $^{13}$C-NMR (125 MHz, CDCl$_3$): δ (ppm) 140.6 (q), 127.9 (t), 127.4 (t), 126.0 (t), 85.0 (t), 84.2 (t), 77.8 (t), 71.6 (t), 62.3 (s)

D. Synthesis of β-D-1-Deoxy-1-phenyl-3,5-O-(1,1,3,3-tetraisopropyldisiloxanylidene)-ribofuranose (Compound A2)

To a cooled (−20° C.) solution of 1,3-dichloro-1,1,3,3-tetraisopropyldisiloxane (1.875 ml, 1.2 eq) in pyridine (48 ml), was slowly added a solution of Compound A1 (1.026 g, 4.88 mmol) in pyridine (48 ml). The temperature was allowed to reach room temperature, and the reaction mixture was stirred overnight at room temperature. The reaction mixture was concentrated in vacuo. Azeotropic rotavapory evaporation with toluene to remove all pyridine yielded the crude product, which was purified by column chromatography (60-230 mesh silica, dichloromethane: ethyl acetate 99:1). This yielded 1.92 g of Compound A2 as a colorless oil (87%).

Formula: 452.73

Molecular weight: $C_{23}H_{40}O_5Si_2$ $R_f$: 0.45 (CH$_2$Cl$_2$: ethyl acetate 99:1) $[\alpha]_D^{20}$=−28.4° C.; $[\alpha]_{365}^{20}$=−96.2° C. (c=0.98 in chloroform) IR (KBr) (cm$^{-1}$): 2945 (s), 2868 (s), 1464 (s); 1386 (m), 1336 (m), 1286 (m), 1247 (m), 1213 (m), 1124 (s), 1065 (s), 1040 (s), 996 (s), 883 (s), 858 (m), 779 (m), 755 (m), 701 (s) ES-MS: 453 [M+H$^+$], 470 [M+NH$_4^+$], 475 [M+Na$^+$] EI-MS: 43 (21), 105 (100), 135 (43), 157 (57), 191 (9), 235 (75), 261 (10), 305 (8), 399 (5), 365 (2), 409 (12), 412 (<1) [M$^+$−43] $^1$H-NMR (500 MHz, CDCl$_3$): δ (ppm) 7.42 (2H, d, J=7.5 Hz), 7.35 (2H, dd, app t, J=7.5 Hz), 7.28 (1H, d, J=7.5 Hz), 4.85 (1H, d, J=3.6 Hz), 4.38 (1H, dd, J=6.9, 6.0 Hz), 4.12 (1H, dd, J=12.3, 3.5 Hz), 4.08 (1H, dd, J=12.3, 4.8 Hz), 4.03 (1H, ddd, J=6.9, 4.8, 3.5 Hz), 3.95 (1H, dd, J=6.0, 3.6 Hz), 2.96 (1H, br s) $^{13}$C-NMR (125 MHz, CDCl$_3$): δ (ppm) 141.5 (q), 129.8 (t), 129.1 (t), 127.2 (t), 86.9 (t), 83.8 (t), 78.7 (t), 73.0 (t), 63.8 (s), 18.9 (p), 18.8 (p), 18.7 (p), 18.6 (p), 18.5 (p), 18.4 (p), 14.8 (t), 14.6 (t), 14.3 (t), 14.1 (t)

E. Synthesis of β-D-1-Deoxy-1-phenyl-2-O-methyl-3,5-O-(1,1,3,3-tetraisopropyldisiloxanylidene)-ribofuranose (Compound A3)

To a solution of Compound A2 (1.73 g, 3.81 mmol) in iodomethane (25 ml) was added silver(I)oxide (1.1 g, 1.25 eq) in 5 portions in a 1 hour interval. The reaction mixture was heated under reflux and after the last addition stirred overnight. Next the reaction mixture was filtered off over celite, and concentrated in vacuo. Then the reaction was repeated under the same conditions as above. The same work-up procedure gave 1.80 g of residue, which was purified using column chromatography (60-230 mesh silica, cyclohexane:ethyl acetate 95:5), yielding 1.68 g of Compound A3 as a white crystalline product (95%).

Formula: $C_{24}H_{42}O_5Si_2$

Molecular weight: 466.76 $R_f$: 0.43 (cyclohexane: ethyl acetate 9:1) $[\alpha]_D^{20}$=−27.6° C.; $[\alpha]_{365}^{20}$=−79.1° C. (c=1.01 in chloroform) Melting point: 35-36° C. IR (KBr) (cm$^{-1}$): 2945 (s), 2868 (s), 1465 (s), 1143 (s), 1073 (s), 1039 (s), 982 (m), 887 (s), 866 (m), 700 (s) ES-MS: 467 [M+H$^+$], 489 [M+Na$^+$] EI-MS: (m/z) 43 (20), 105 (52), 157 (60), 175 (9), 205 (5), 249 (100), 277 (4), 319 (6), 391 (8), 423 (10), 467 (<1) [M$^+$] $^1$H-NMR (500 MHz, CDCl$_3$): δ (ppm) 7.44 (2H, d, J=7.4 Hz), 7.33 (2H, dd, app t, J=7.4 Hz), 7.25 (1H, d, J=7.4 Hz), 4.97 (1H, s), 4.38 (1H, dd, J=8.6, 4.9 Hz), 4.21 (1H, dd, J=13.4, 2.7 Hz), 4.05-4.02 (2H, m), 3.59 (3H, s), 3.57-3.56 (1H, m), 1.11-0.99 (28H, m) $^{13}$C-NMR (125 MHz, CDCl$_3$): δ (ppm) 142.5 (q), 129.8 (t), 128.9 (t), 127.1 (t), 88.5 (t), 86.0 (t), 82.3 (t), 71.8 (t), 62.0 (s), 60.3 (p), 19.0 (p), 18.8 (p), 18.7 (p), 18.6 (p), 18.5 (p), 18.4 (p), 14.9 (t), 14.5 (t), 14.3 (t), 14.0 (t)

F. Synthesis of β-D-1-Deoxy-1-phenyl-2-O-methyl-ribofuranose (Compound A4)

To a solution of Compound A3 (1.56 g, 3.34 mmol) in dry THF (25 ml) was added a solution of tetra-n.butylammoniumfluoride (8.35 ml, 1M sol. in THF, 2.5 eq). The reaction mixture was stirred overnight at room temperature. The reaction was worked up by evaporating the solvent in vacuo, to give 4 g of a soap-like residue. Purification by column chromatography (60-230 mesh silica, dichloromethane: ethyl acetate 1:1) yielded 742 mg of Compound A4 as white crystals (99%).

Formula: $C_{12}H_{16}O_4$

Molecular weight: 224.25 $R_f$: 0.18 (CH$_2$Cl$_2$: ethyl acetate 1:1) $[\alpha]_D^{20}$=+17.6° C.; $[\alpha]_{365}^{20}$=+47.5° C. (c=1.01 in chloroform) Melting point: 73-74° C. IR (KBr) (cm$^{-1}$): 3409 (s), 3062 (m), 3032 (m), 2930 (s), 2835 (m), 1457 (m), 1200 (m), 1120 (s), 1083 (s), 1053 (s), 1028 (s), 992 (m), 760 (m), 700 (s) ES-MS: 247 [M+Na$^+$] EI-MS: (m/z) 51 (8), 71 (13), 87 (100), 91 (24), 115 (4), 134 (6), 147 (1), 175 (3), 192 (5), 193 (6) [M$^+$−31] $^1$H-NMR (500 MHz, CDCl$_3$) δ (ppm) 7.38-7.35 (4H, m), 7.33-7.29 (1H, m), 4.86 (1H, d, J=5.6 Hz), 4.22 (1H, dd, app t, J=5.6 Hz), 4.03-4.00 (1H, m), 3.96 (1H, dd, J=12.0, 3.1 Hz), 3.81 (1H, dd, J=12.0, 4.3 Hz), 3.65 (1H, dd, app t, J=5.6 Hz), 3.44 (1H, s) $^{13}$C-NMR (125 MHz, CDCl$_3$):

δ (ppm) 141.2 (q), 130.1 (t), 129.5 (t), 127.5 (t), 87.9 (t), 85.9 (t), 84.3 (t), 72.0 (t), 64.3 (s), 60.0 (p)

G. Synthesis of β-D-1-Deoxy-1-phenyl-2-O-methyl-3,5-O-benzylidene-ribose (Compound A5)

To a solution of Compound A4 (100 mg, 0.446 mmol) in pyridine (4.35 ml) was added dropwise α,α-dibromotoluene (111 µl, 1.5 eq). The reaction mixture was stirred at room temperature for 1 hour and then heated to reflux, and stirred as-such overnight. Next 3.5 eq of α,α-dibromotoluene was added in 3 portions (1, 1.5, 1) in a 1 day-interval, while monitoring the reaction by TLC. After the last addition, the reaction mixture was stirred at reflux temperature for 3 days. Reaction work-up was started by the addition of diethyl ether, followed by stirring for 15 min. Next the reaction mixture was filtered over a short silica plug, and the filter was rinsed with diethyl ether until 100 ml of filtrate was obtained. This organic phase was washed with $H_2O$ (2×75 ml) and brine (75 ml). Drying over $MgSO_4$, azeotropic rotavapory evaporation with toluene to remove traces of pyridine, and drying in vacuo, yielded 146 mg of residue. Purification by column chromatography (230-400 mesh silica, cyclohexane: ethyl acetate 92:8) yielded 37 mg of Compound A5 as a white crystalline product (27%).

Formula: $C_{19}H_{20}O_4$

Molecular weight: 312.36 $R_f$: 0.25 (cyclohexane: ethyl acetate 92:8) $[\alpha]_D^{20}=-37.3°$ C.; $[\alpha]_{365}^{20}=-74.2°$ C. (c=0.95 in chloroform) Melting point: 94-95° C. IR (KBr) (cm$^{-1}$): 2898 (m), 1454 (m), 1375 (m), 1210 (m), 1141 (s), 1109 (m), 1079 (s), 1047 (s), 1027 (s), 1000 (s), 963 (s), 759 (m), 743 (m), 698 (s) API-MS: 313 [M+H$^+$] EI-MS: (m/z) 57 (68), 77 (32), 105 (58), 107 (42), 149 (23), 163 (100), 180 (12), 200 (3), 238 (2), 260 (2), 277 (2), 291 (5), 312 (<1) [M$^+$] $^1$H-NMR (500 MHz, CDCl$_3$): δ (ppm) 7.52-7.50 (2H, m), 7.41-7.34 (7H, m), 7.31-7.24 (1H, m), 5.67 (1H, s), 4.96 (1H, s), 4.58 (1H, dd, J=9.4, 4.4 Hz), 4.03 (1H, dd, app t, J=10.1, 9.4 Hz), 3.94 (1H, ddd, app dt, J=10.1, 9.5, 4.4 Hz), 3.85 (1H, d, J=4.6 Hz), 3.73 (1H, dd, J=9.5, 4.6 Hz), 3.51 (3H, s) $^{13}$C-NMR (125 MHz, CDCl$_3$): δ (ppm) 141.3 (q), 138.9 (q), 129.6 (t), 129.2 (t), 128.8 (t), 128.4 (t), 127.3 (t), 126.7 (t), 103.0 (t), 87.7 (t), 85.4 (t), 82.8 (t), 72.1 (s), 70.8 (t), 58.3 (p)

H. Synthesis of D-1,2-dideoxy-1-oxo-ribofuranose (Compound 2.1) (generally following Wichai, U.; Woski, S. A.; *Orz. Lett.*, 1999, 1(8), 1173-1175)

To a solution of 2-deoxy-D-ribose (2.13 g, 16.0 mmol) in $H_2O$ (12.8 ml) was carefully added $Br_2$ (4.3 ml). The reaction vessel was thoroughly sealed and the mixture was stirred under Ar-atmosphere at room temperature for 23 hours. Reaction work-up was started by addition of $Ag_2CO_3$ and the resulting precipitation of AgBr, followed by filtration. This procedure was repeated until pH=7. The filtrate was concentrated in vacuo, followed by azeotropic removal of water with toluene. This yielded 2.15 g residue as a yellow oil (Compound 2.1), which was used in the next reaction without further purification.

Formula: $C_5H_8O_4$

Molecular weight: 132.11

I. Synthesis of D-1,2-dideoxy-1-oxo-3,5-O-(1,1,3,3-tetraisopropyldisiloxanylidene)-ribofuranose (Compound 2.2)) (generally following Wichai, U.; Woski, S. A.; *Orz. Lett.*, 1999, 1(8), 1173-1175)

To a solution of crude Compound 2.1, (theoretical 2.11 g, 16.0 mmol, real weight: 2.16 g) in dry DMF (40 ml) was added imidazole (2.61 g, 2.4 eq). Subsequently 1,3-dichloro-1,1,3,3-tetraisopropyldisiloxane (6.15 ml, 1.2 eq) was added. The reaction mixture was stirred overnight at room temperature under Ar-atmosphere. The reaction was stopped by pouring out the mixture into water (100 ml). Extraction with $Et_2O$ (3×75 ml), washing of the combined organic layers with saturated $NaHCO_3$ (100 ml) and brine (100 ml), drying on $MgSO_4$, filtration and concentration in vacuo, yielded 7.05 g as a yellow oil. Purification by column chromatography (60-230 mesh silicagel, $CH_2Cl_2$) yielded 4.39 g product (Compound 2.2) as a colorless oil (73% yield over 2 steps).

Formula: $C_{17}H_{34}O_5Si_2$

Molecular weight: 374.62 $R_f$: 0.54 ($CH_2Cl_2$) $[\alpha]_D^{20}=+14.2°$; $[\alpha]_{365}^{20}=+60.5°$ (c=1.06 in chloroform) IR(KBr) 2946 (s), 2894 (m), 2872 (s), 1797 (s), 1465 (m), 1240 (m), 1200 (m), 1167 (m), 1128 (s), 1074 (m), 1055 (s), 1035 (s), 992 (m), 883 (m), 698 (m) cm$^{-1}$ EI-MS: (m/z) 43 (14), 105 (14), 135 (20), 175 (9), 203 (5), 259 (7), 289 (5), 331 (100) [M$^+$−43] $^1$H-NMR (500 MHz, CDCl$_3$): δ 4.82-4.77 (1H, m); 4.22 (1H, ddd, app. dt, J=6.8, 3.5 Hz), 4.11 (1H, dd, J=12.2, 3.5 Hz), 4.01 (1H, dd, J=12.2, 6.8 Hz), 2.89 (1H, dd, J=17.0, 8.0 Hz), 2.70 (1H, J=17.0, 9.2 Hz), 1.19-0.94 (28H, m) APT-NMR (125 MHz, CDCl$_3$): δ 173.0 (C), 85.1 (CH), 70.8 (CH), 63.3 (CH$_2$), 38.2 (CH$_2$), 17.9 (CH$_3$), 17.7 (CH$_3$), 17.6 (CH$_3$), 17.4 (CH$_3$), 14.0 (CH), 13.9 (CH), 13.4 (CH), 13.3 (CH)

J. Synthesis of α-β-D-2-deoxy-1-phenyl-3,5-O-(1,1,3,3-tetraisopropyldisiloxanylidene)-ribofuranose (Compound 2.3)

To a solution of Compound 2.2 (4.27 g, 11.4 mmol) in dry THF (105 ml), cooled to −78° C., was added drop-wise over 10 min phenyllithium (9.5 ml, 1.8M-sol in cyclohexane: ether 7:3, 1.5 eq). The reaction mixture was stirred at −78° C. under Ar-atmosphere for 1 hour. Next the reaction was quenched by adding saturated $NH_4Cl$-sol. (250 ml) and diluting with $Et_2O$ (100 ml). Subsequently layers were separated and the aqueous layer was extracted with $Et_2O$ (3×250 ml). The combined organic layers were washed with sat. $NH_4Cl$-sol (500 ml) and brine (500 ml), filtrated and concentrated in vacuo. This yielded a yellow oil (Compound 2.3) which was used in the next reaction without further purification.

Formula: $C_{23}H_{40}O_5Si_2$

Molecular weight: 452.73

K. Synthesis of α-β-D-1,2-dideoxy-1-phenyl-3,5-O-(1,1,3,3-tetraisopropyldisiloxanylidene)-ribofuranose (Compound A6A+B) (generally following Thiem, J.; Duckstein, V.; Prahst, A.; Matzke, M.; *Liebigs Ann. Chem.*, 1987, 289-295)

To a solution of crude Compound 2.3 (theoretical 11.4 mmol) in dry $CH_2Cl$ (47 ml), cooled to −78° C. and under Ar-atmosphere, were added drop-wise triethylsilane (5.47 ml, 3 eq), and $BF_3.Et_2O$ (4.33 ml, 3 eq). Stirring was continued at −78° C. for 4 hours. The reaction was quenched by adding sat. $NaHCO_3$-sol. Layers were separated and the aqueous layer was extracted with $Et_2O$ (3×150 ml). The combined organic layers were washed with sat. $NaHCO_3$-sol. (150 ml), $H_2O$ (150 ml) and brine (150 ml). Drying on $MgSO_4$, filtration and concentration in vacuo yielded 5.16 g residue as a yellow oil. Purification by column chromatography (60-230 mesh silicagel, toluene) gave a residue with a pink color. Stirring on charcoal and filtration over celite yielded 2.70 g colorless oil as an inseparable mixture of epimers Compound A6A and Compound A6B. NMR-analysis revealed that the α:β ratio was 15:85.

Formula: $C_{23}H_{40}O_4Si_2$

Molecular weight: 436.73 $R_f$: 0.45 (toluene)

L. Synthesis of α-β-D-1,2-dideoxy-1-phenyl-ribofuranose (Compound 2.4) (generally following Wichai. U. and Wosoki, S. A.; *Org., Lett.*, 1999, 1(8),1173-1175)

To a solution of the mixture Compound A6A and Compound A6B (2.62 g, 6.0 mmol) in dry THF (45 ml), was added a solution of TBAF (15 ml, 1M-sol.) in THF. The reaction mixture was stirred at room temperature under Ar-atmosphere for 2 hours. Subsequently the reaction mixture was concentrated under reduced pressure, to yield 7.54 g residue as an orange oil. This was first purified by column chromatography (60-230 mesh silicagel, $CH_2Cl_2:CH_3OH$ 9:1), and secondly again by column chromatography (60-230 mesh silicagel, gradient: $CH_2Cl_2$, $CH_2Cl_2$:iPrOH 96:4, 92:8, 9:1, 84:16). This yielded 1.05 g yellow-white solid (Compound 2.4) as inseparable mixture of epimers (total yield 90%).

Formula: $C_{11}H_{14}O_3$

Molecular weight: 194.23 $R_f$: 0.30 ($CH_2Cl_2:CH_3OH$ 9:1)

M. Synthesis of β-D-1,2-dideoxy-1-phenyl-ribofuranose-3,5-diacetate (Compound A7)

To a solution of Compound 2.4 (1.04 g, 5.35 mmol, mixture of epimers) in dry pyridine (40 ml) was added acetic anhydride (14 ml) and DMAP (65 mg, 0.1 eq). Stirring was continued at room temperature overnight. Next the reaction mixture was poured out into a saturated $NaHCO_3$-sol. (200 ml) and diluted with EtOAc (100 ml). Layers were separated and the organic layer was washed with 1N HCl-sol. (4×100 ml) and brine (100 ml). Drying on $MgSO_4$, filtration and concentration in vacuo yielded an orange oil which was purified by repeated column chromatography (230-400 mesh silica, pentane:ether 6:4), to yield 1.06 g pure β-epimer (71%) and 197 mg α/β mixture (13%) (Compound A7). It was impossible to obtain pure α.

Formula: $C_{15}H_{18}O_5$

Molecular weight: 278.30 $R_f$: 0.22 (pentane/ether 6:4) $[α]_D^{20}=+21.4°$; $[α]_{365}^{20}=+65.3°$ (c=1.06 in $CHCl_3$) IR(KBr): 1742 (s), 1454 (m), 1240 (s), 1179 (m), 1100 (m), 1054 (s), 1012 (m), 946 (m), 755 (m) 701 (m) cm$^{-1}$ EI-MS: 43 (100), 77 (17), 78 (9), 105 (63), 145 (14), 158 (17), 176 (4), 205 (2), 218 (2), 235 (<1), 250 (<1), 278 (2) [M$^+$] ES-MS: 279=[M+H]$^+$ $^1$H-NMR (500 MHz, $CDCl_3$): δ (ppm) 7.37-7.34 (4H, m), 7.31-7.27 (1H, m), 5.23 (1 H, d, J 6.2 Hz), 5.11 (1H, dd, J=10.9, 5.1 Hz), 4.43-4.37 (1H, m), 4.28-4.23 (1H, m), 2.34 (1H, dd, J=13.8, 5.1 Hz), 2.13 (3H, s), 2.09 (3H, s), 2.07 (1H, ddd, J=13.8, 10.9, 6.2 Hz)

APT-NMR (125 MHz, $CDCl_3$): δ (ppm) 170.8 (C), 170.6 (C), 140.6 (C), 128.5 (CH), 127.9 (CH), 125.8 (CH), 82.6 (CH), 80.7 (CH), 76.6 (CH), 64.4 ($CH_2$), 41.3 ($CH_2$), 21.1 ($CH_3$), 20.9 ($CH_3$)

N. Synthesis of β-D-1,2-dideoxy-1-phenyl-ribofuranose (Compound A8)

To a solution of Compound A7 (812 mg, 3.21 mmol) in methanol (16 ml) and THF (16 ml) was added $K_2CO_3$ (111 mg, 0.25 eq). The reaction mixture was stirred at room temperature under Ar-atmosphere. After 5 hours the reaction mixture was concentrated under reduced pressure, to give 757 mg residue as a white foam. This was purified by column chromatography (230-400 mesh silica, $CH_2Cl_2$:$CH_3OH$ 9:1) to yield 616 mg pure Compound A8 as a white solid (99%).

Formula: $C_{11}H_{14}O_3$

Molecular weight: 194.23 $R_f$: 0.30 ($CH_2Cl_2$:$CH_3OH$ 9:1) Melting point: 89-91° C. $[α]_D^{20}=+50.0°$; $[α]_{365}^{20}=+157.9°$ (c=0.99 in $CH_3OH$) IR (KBr) 3360 (s), 2935 (m), 2885 (m), 1455 (m), 1091 (m), 1048 (s), 1001 (m), 942 (m), 75 (m), 697 (s), 667 (m), 583 (m) cm$^{-1}$ EI-MS: 51 (30), 77 (54), 91 (100), 105 (68), 117 (72), 120 (23), 134 (11), 145 (20), 163 (10), 176 (3), 194 (17) [M$^+$] $^1$H-NMR (500 MHz, $CDCl_3$): δ (ppm) 7.39-7.28 (5H, m), 5.18 (1H, dd; J=10.2, 5.6 Hz), 4.46 (1H, m), 4.02 (1H, ddd, J=7.7, 4.3, 1.1 Hz), 3.86-3.72 (2H, m), 2.27 (1H, ddd, J=13.3, 5.6, 1.9 Hz), 2.10-2.00 (3H, m) APT-NMR (125 MHz, $CDCl_3$): δ (ppm) 142.5 (C), 130.0 (CH), 129.3 (CH), 127.5 (CH), 88.7 (CH), 81.6 (CH), 75.2 (CH), 64.1 ($CH_2$), 45.4 ($CH_2$)

O. Synthesis of α-D-1,2-O-isopropylidene-xylofuranose (Compound 3.1) (generally following Larsen, C. H., Ridgeway, B. H., Shaw, J. T., Woerpel, K. A.: *J. Am. Chem. Soc.*, 1999, 121, 12208-9)

To a mixture of D-xylose (5.0 g, 33.3 mmol) in acetone (70 ml), were added $CuSO_4$.anh (6.64 g, 1.25 eq), and concentrated $H_2SO_4$-(500 μl, 0.135 eq). The reaction mixture was stirred at room temperature under Ar-atmosphere during 24 hours. Next the reaction mixture was filtered, neutralized with ammonia, again filtered and concentrated under reduced pressure. The residue, a yellow oil, was dissolved in MeOH (HPLC, 100 ml). To this solution a 0.1 M HCl-sol. (12.5 ml) was added, and the resulting mixture was stirred at 40° C. under Ar-atmosphere for 4 hours. The reaction mixture was then neutralized by adding solid $NaHCO_3$. Filtration, concentration in vacuo and azeotropic removal of water with EtOH/toluene (1/1) gave a residue which was dissolved in $CH_2Cl_2$, dried on $MgSO_4$, filtered and concentrated in vacuo. The so obtained yellow oil (7.16 g) was purified by column chromatography (230-400 mesh silicagel, $CH_2Cl_2$:$CH_3OH$ 95:5), to yield 5.73 g Compound 3.1 as a white solid (91%).

Formula: $C_8H_{14}O_5$

Molecular weight: 190.19 $R_f$: 0.19 ($CH_2Cl_2$:$CH_3OH$ 95:5) $[α]_D^{20}=-14.6°$; $[α]_{365}^{20}=-52.2°$ (c=0.99 in $CHCl_3$) Melting point: 41-42° C. IR (KBr): 3383 (br s), 2987 (m), 2937 (m), 1376 (m), 1255 (m), 1217 (m), 1164 (m), 1104 (m), 1073 (s), 1013 (s), 859 (m) cm$^{-1}$ EI-MS: (m/z) 43 (62), 59 (100), 74 (19), 85 (33), 101 (7), 115 (5), 127 (14), 149 (3), 159 (11), 175 (29) ES-MS: 191=[M+H]$^+$ $^1$H-NMR (500 MHz, $CDCl_3$): δ (ppm) 5.88 (1H, d, J=3.7 Hz), 4.46 (1H, d, J=3.7 Hz), 4.16 (1H, ddd, J=6.4, 5.1, 2.8 Hz), 4.11 (1H, d, J=2.8 Hz), 3.80 (1H, dd, J=11.6, 5.1 Hz), 3.74 (1H, dd, J=11.6, 6.4 Hz), 1.45 (3H, s), 1.29 (3H, s)

APT-NMR (125 MHz, $CDCl_3$): δ (ppm) 112.6 (C), 106.3 (CH), 86.9 (CH), 82.4 (CH), 75.8 (CH), 61.0 ($CH_2$), 27.0 ($CH_3$), 26.4 ($CH_3$)

P. Synthesis of α-D-1,2-O-isopropylidene-3,5-O-dibenzyl-xylofuranose (Compound A9)

To a solution of Compound 3.1 (5.61 g, 29.5 mmol) in dry DMF (130 ml), cooled to 0° C. and under Ar-atmosphere, NaH (2.83 g of a 60% dispersion, 4 eq) was added carefully. The reaction mixture was stirred at 0° C. for 30 minutes, after which benzylbromide (17.5 ml, 5 eq) was added. The reaction mixture was stirred at 0° C. for 15 min, and then allowed to reach room temperature. After stirring as such overnight, the mixture was poured out into water (650 ml) and extracted with $Et_2O$ (3×500 ml). Washing of the combined organic layers with brine (750 ml), drying on $MgSO_4$, filtration and concentration in vacuo, yielded 15.95 g residue as an orange oil. Purification by column chromatography (230-400 mesh silica, pentane:ether 75:25) yielded 10.45 g Compound A9 as a colorless oil (96%).

Formula: $C_{22}H_{26}O_5$

Molecular weight: 370.44 $R_f$: 0.24 (pentane:ether 75:25) $[α]_D^{20}=53.5°$; $[α]_{365}^{20}=-171.80°$ (c=1.07 in $CHCl_3$) IR (KBr): 2925 (m), 1454 (m), 1373 (m), 1214 (m), 1165 (m), 1076 (s), 1019 (s), 737 (m), 698 (m) cm$^{-1}$ EI-MS: (m/z) 43

(11), 91 (100), 107 (4), 133 (2), 163 (2), 279 (3), 370 (<1)[M$^+$] ES-MS: 371=[M+H]$^{+1}$H-NMR (500 MHz, CDCl$_3$): δ (ppm) 7.34-7.26 (10H, m), 5.88 (1H, d, J=3.8 Hz), 4.66 (1H, d, J=12.0 Hz), 4.61 (1H, d, J=12.0 Hz), 4.60

(HIV), Herpes Simplex Virus (HSV), Vaccinia Virus (VV), the Varicella Zoster Virus (VZV) and the human Cytomegalovirus (CMV).

The results are presented in Table 2.

TABLE 2

Antiviral activity of the compounds

| Compound | EC$_{50}$ (μg/ml)$^a$ | | | | | | | IC$_{50}$ (μg/ml)$^b$ CMV | |
|---|---|---|---|---|---|---|---|---|---|
| | HIV-1 (III$_B$) (CEM) | HIV-2 (ROD) (CEM) | HSV-1 (KOS) (E$_6$SM) | HSV-2 (G) (E$_6$SM) | VV (E$_6$SM) | VZV (HEL) OKA | 07/1 | AD-169 Strain | David Strain |
| Compound A1 | >100 | >100 | >400 | >400 | >400 | >50 | >50 | >50 | >50 |
| Compound A2 | >4 | >4 | >3.2 | >3.2 | >3.2 | >2 | >2 | 1.2 | 2 |
| Compound A3 | >4 | >4 | >16 | >16 | >16 | >2 | >2 | 1.3 | 1.3 |
| Compound A4 | >100 | >100 | >400 | >400 | >400 | >50 | >50 | >50 | >50 |
| Compound A5 | N.A.$^c$ | N.A. | N.A. | N.A. | N.A. | N.A. | N.A. | N.A. | N.A. |
| Compound A6 A + B | N.A. | N.A. | N.A. | N.A. | N.A. | N.A. | N.A. | N.A. | N.A. |
| Compound A7 | N.A. | N.A. | >400 | >400 | >400 | N.A. | N.A. | >100 | >100 |
| Compound A8 | N.A. | N.A. | >400 | >400 | >400 | N.A. | N.A. | >100 | >100 |
| Compound A9 | N.A. | N.A. | >80 | >80 | 48 | >80 | >80 | 10.5 | 7.6 |

$^a$50% effective concentration or compound concentration required to inhibit HIV-induced cytopathicity in human CEM cell cultures, HSV- and VV-induced cytopathicity in human embryo fibroblast E$_6$SM, and VZV-induced plaque formation in human embryonic lung HEL cell cultures by 50%
$^b$inhibitory concentration required to reduce virus plaque formation by 50. Virus input was 100 plaque-forming units (PFU)
$^c$Not available (1H, d, J=3.8 Hz), 4.53 (1H, d, J=12.0 Hz), 4.51 (1H, d, J=12.0 Hz), 4.41 (1H, ddd, app. dt, J=6.1, 3.2 Hz), 3.98 (1H, d, J=3.2 Hz), 3.78 (1H, dd, J=9.9, 6.2 Hz), 3.75 (1H, dd, J=9.9, 6.1 Hz), 1.49 (3H, s), 1.32 (3H, s) APT-NMR (125 MHz, CDCl$_3$): δ (ppm) 138.0 (C), 137.5 (C), 128.3 (CH), 128.3 (CH), 127.8 (CH), 127.7 (CH), 127.6 (CH), 127.5 (CH), 111.6 (C), 105.0 (CH), 82.3 (CH), 81.7 (CH), 79.1 (CH), 73.4 (CH$_2$), 71.9 (CH$_2$), 67.5 (CH$_2$), 26.7 (CH$_3$), 26.2 (CH$_2$)

Biological Activity (generally following Balows, A.; Hausler, W. J. Jr.; Herrmann, K. L.; Isenberg, H. D.; Shadonmy, H. J.; *Manual of Clinial Microbiology Fifth Edition*)

1. Antiviral Activity

For determination of antiviral activity against CMV, human embryonic lung fibroblast (HEL) cells grown in 96-well microplates were infected with 20 PFU virus/well. After 2 h of incubation at 37° C., the infected cells were replenished with 0.1 ml of medium containing serial dilutions of the test compound. On day 7 the plaques were counted microscopically after staining the cells with Giemsa's solution. The minimum antiviral concentration was expressed as the dose required to inhibit virus-induced plaque formation by 50%.

The new compounds were screened against various pathogenic viruses such as the Human Immunodeficiency Virus No relevant activity was observed against HIV or HSV. Compound A9 showed a slight activity against VV. Compound A5 showed a slight and Compound A2, Compound A3 and Compound A9 did show a significant activity against CMV.

2. Antitumor Activity

The compounds were tested for antitumor activity via the inhibitory effects on the proliferation of murine leukemia cells (L1210/0), murine mammary carcinoma cells (FM3A) and human T-lymphocyte cells (Molt4/C8), (CEM/0). The results are presented in Table 4. It can be seen that Compound A2 and Compound A3 show a small cytostatic activity. Compound A1 and Compound A4 show no effect at concentrations up to 200 ppm.

TABLE 4

Cytostatic activity of the compounds

| | IC50(μg/ml)$^a$ | | | |
|---|---|---|---|---|
| Compound | L1210/0 | FM3A/0 | Molt4/C8 | CEM/0 |
| Compound A1 | >200 | >200 | >200 | >200 |
| Compound A2 | 16 ± 1 | 16 ± 2 | 15 ± 1 | 15 ± 1 |
| Compound A3 | 18 ± 0.5 | 15 | 19 ± 2 | 20 ± 4 |
| Compound A4 | >200 | >200 | >200 | >200 |
| Compound A5 | N.A. | N.A. | N.A. | N.A. |
| Compound A6 A + B | N.A. | N.A. | N.A. | N.A. |

TABLE 4-continued

Cytostatic activity of the compounds

| Compound | IC50(μg/ml)[a] | | | |
|---|---|---|---|---|
| | L1210/0 | FM3A/0 | Molt4/C8 | CEM/0 |
| Compound A7 | N.A. | N.A. | N.A. | N.A. |
| Compound A8 | N.A. | N.A. | N.A. | N.A. |
| Compound A9 | N.A. | N.A. | N.A. | N.A. |

[a] 50% inhibitory concentration

3. Antibacterial and Antifungal Activity (generally following Reference Method for Broth Dilution Antifungal Susceptibility Testing of Yeast; Approved Standard, NCCLS document M27-A, 17 (9); Reference for Dilution Antimicrobial Susceptibility Tests for Bacteria That Grow Aerobically—Fourth Edition; Approved Standard, NCCLS document M7-A4; 18 (13); and Reference Method for Broth Dilution Antifungal Susceptibility Testing of Conidium-Forming Filamentous Fungi; Proposed Standard, NCCLS document M38-P, 18 (13))

For the determination of the antibacterial and antifungal activity we use the BioScreen C Analyzer (Labsystems), which is an automated reader-incubator. It measures growth continuously by vertical photometry (optical density), processes the data and provides a print out of the results. The area under the growth curve can be determined via the Biolink software. The area of the control run (without microorganisms) is being subtracted from the sample area, resulting in a number, which can be compared with the reference or golden standards. This number gives us an indication of the biological activity of the molecules tested and can be expressed as a % of growth at a specific dose compared to a negative control which has a value of 100.

The inoculum size of the bacteria is standardized to 5×10[5] CFU/ml. The 100-honey-well plates with bacteria in Mueller-Hinton broth are incubated at 35° C. for 16 hours, yeasts are incubated 35° C. for 24 hours (*C. albicans*) or 48 hours (*C. neoformans*) in RPMI 1640+MOPS buffer at 165 mM. Moulds also in RPMI 1640+MOPS buffer at 165 mM are incubated at 30° C. for 3 days (*A. fumigatus*) or –5 days (T mentagrophytes).

As a control, all microorganisms are screened against some reference antibiotics with known MIC data (Table 3).

TABLE 3

Microorganisms and antibiotics used as a control

| Microorganism | Reference antibiotic |
|---|---|
| Gram +; *Staphylococcus aureus* | Vancomycin |
| Gram −; *Pseudomonas aeruginosa* | Gentamicin |
| Fungi | Amphotericin B |

The dose used for all new molecules in all tests is 25 μg/ml. The results of the antibacterial activities are depicted in Table 5. The microorganisms used are *Staphylococcus aureus, Enterococcus faecalis, Pseudomonas aeruginosa, Escherichia coli* and *Clostridium perfringens*. In Table 6 the results of the antifungal screenings are given for the new molecules. The microorganisms used were *Candida albicans, Cryptococcus neoformans* (both yeasts), *Trichophyton mentagrophytes* and *Aspergillus fumigatus* (molds).

TABLE 5

Antibacterial activity of the compounds

% of growth at 25 PPM compared to negative control

| Compound | E. faecalis ATCC 29212 LMG 8222 | S. aureus ATCC 29213 LMG 10147 | P. aeruginosa ATCC 27853 LMG 16217 | E. coli ATCC 25922 | C. perfringens ATCC 13124 |
|---|---|---|---|---|---|
| Negative control | 100 | 100 | 100 | 100 | 100 |
| Compound A1 | 96.0 | 96.7 | 92.7 | 93.4 | N.A. |
| Compound A2 | 86.4 | 74.4 | 87.2 | 93.0 | N.A. |
| Compound A3 | 94.2 | 92.5 | 87.6 | 91.3 | N.A. |
| Compound A4 | 95.4 | 96.9 | 93.5 | 92.8 | N.A. |
| Compound A5 | 92.0 | 92.0 | 91.0 | 124.0 | 95.0 |
| Compound A6 A + B | 95.0 | 95.0 | 92.0 | 94.0 | 98.0 |
| Compound A7 | 98.1 | 91.2 | 92.7 | 94.8 | 95.4 |
| Compound A8 | 95.5 | 92.3 | 92.7 | 99.2 | 96.2 |
| Compound A9 | 101.8 | 93.7 | 93 | 95.6 | 95.1 |

TABLE 6

Antifungal activity of the compounds

% of growth at a dose of 25 PPM compared to the negative control

| Compound | Candida albicans ATCC 24433 IHEM 10284 | T. mentagrophytes ATCC 9233 IHEM 10342 | A. fumigatus IHEM 2895 | C. neoformans ATCC 90112 IHEM 9558 |
|---|---|---|---|---|
| Negative control | 100 | 100 | 100 | 100 |
| Compound A1 | 89.2 | 62.4 | 105.9 | 93.3 |
| Compound A2 | 97.5 | 67.6 | 82.0 | 91.9 |
| Compound A3 | 62.2 | 64.4 | 37.5 | 81.1 |
| Compound A4 | 109.7 | 79.7 | 70.9 | 99.9 |
| Compound A5 | 120.0 | 66.0 | 57.0 | 76.0 |
| KPE00001114 | 85.0 | 56.0 | 54.0 | 102.0 |
| Compound A7 | 83.4 | 83.0 | 95.0 | 67.8 |
| Compound A8 | 92.4 | 95.0 | 107.0 | 84.8 |
| Compound A9 | 85.9 | 92 | 74 | 55.1 |

Out of the screenings can be concluded that the synthesized new carbohydrate derivatives show no significant antibacterial and antifungal effect.

SUMMARY

After a series of 6-membered bicyclic carbohydrate derivatives the analogues were made with a 5-membered carbohydrate (D-ribofuranose in this specific case). The study of the biological activity against viruses, bacteria, fungi and tumor cell lines revealed that also in this series some molecules possessed a highly-selective antiviral activity, mainly against CMV. However, no significant antifungal or antibacterial activity was observed for any of the synthesized molecules. However, the results establish tha 5-membered bicyclic carbohydrates show antiviral activity.

The foregoing description and drawings comprise illustrative embodiments of the present inventions. The foregoing embodiments and the methods described herein may vary based on the ability, experience, and preference of those skilled in the art. Merely listing the steps of the method in a certain order does not constitute any limitation on the order of the steps of the method. The foregoing description and drawings merely explain and illustrate the invention, and the invention is not limited thereto, except insofar as the claims are so limited. Those skilled in the art who have the disclosure before them will be able to make modifications and variations therein without departing from the scope of the invention.

We claim:

1. A method of treating an infection caused by herpesviridae or vaccinia virus in a mammalian subject in need thereof comprising administering to said subject an effective amount of at least one compound according to the formula wherein $R_1$ is selected from the group consisting of alkyl, aryl, O-aryl, S-aryl, OH, O-alkyl, SH, S-alkyl, $NH_2$, $N_3$, halogens, —OOCH, and COOH;

wherein $R_2$ is selected from the group consisting of H, hydroxyl, aliphatic and aromatic ethers and esters;

wherein $R_3$ is selected from the group consisting of alkyl, aryl, O-aryl, S-aryl, OH, O-alkyl, SH, S-alkyl, $NH_2$, $N_3$, halogens, —OOCH, COOH, siloxane rings, and acetal rings; and wherein $R_4$ is selected from the group consisting of alkyl, aryl, O-aryl, S-aryl, OH, O-alkyl, SH, S-alkyl, $NH_2$, $N_3$, halogens, —OOCH, COOH, siloxane rings, and acetal rings.

2. A method as defined in claim 1, wherein $R_1$ is phenyl; $R_2$ is selected from the group consisting of —OMe, —OH, and —H; $R_3$ is selected from the group consisting of —OH, —OAc, —OH, and —OBn; and $R_4$ is selected from the group consisting of —H, —OAc, and —OBn; or a pharmaceutically active derivative thereof.

3. A method as defined in claim 1, wherein the herpesviridae virus is human cytomegalovirus, wherein $R_1$ and $R_2$ form a ring comprising —OC($CH_3$)$_2$O— and wherein $R_3$ and $R_4$ are each —OBn.

4. A method of treating an infection caused by human cytomegalovirus in a mammalian subject in need thereof comprising administering to said subject an effective amount of at least one compound as defined in claim 1, wherein $R_3$ and $R_4$ form a ring comprising a moiety preferably selected from the group consisting of —OSi(i-Pr)$_2$OSi(i-Pr)$_2$O— and —OCH(Ph)O—.

5. A method as defined in claim 4, wherein when $R_3$ and $R_4$ form a ring comprising —OSi(i-Pr)$_2$OSi(i-Pr)$_2$O—, $R_1$ is —Ph, and $R_2$ is selected from the group consisting of —OH and —OMe.

6. A method as defined in claim 4, wherein when $R_3$ and $R_4$ form a ring comprising —OCH(Ph)O—, $R_1$ is —Ph, and $R_2$ is —OMe.

* * * * *